(12) United States Patent
Wang et al.

(10) Patent No.: US 7,996,988 B2
(45) Date of Patent: Aug. 16, 2011

(54) METHOD OF MAKING A PLURALITY OF CALIBRATION-ADJUSTED SENSORS

(75) Inventors: Yi Wang, San Ramon, CA (US);
Benjamin J. Feldman, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 287 days.

(21) Appl. No.: 12/463,192

(22) Filed: May 8, 2009

(65) Prior Publication Data

US 2009/0229122 A1    Sep. 17, 2009

Related U.S. Application Data

(60) Continuation of application No. 11/981,124, filed on Oct. 30, 2007, now Pat. No. 7,895,740, which is a division of application No. 11/461,725, filed on Aug. 1, 2006, now Pat. No. 7,866,026.

(51) Int. Cl.
*H05K 3/02* (2006.01)
*H05K 3/10* (2006.01)
(52) U.S. Cl. .................. 29/846; 29/831; 29/835; 29/847
(58) Field of Classification Search .................... 29/846, 29/831, 835, 847, 849, 874, 882; 204/345, 204/347, 365; 600/403.01, 403.04, 403.11
See application file for complete search history.

(56) References Cited

U.S. PATENT DOCUMENTS

| | | | |
|---|---|---|---|
| 5,762,770 A | 6/1998 | Pritchard et al. | |
| 5,997,817 A | 12/1999 | Crismore et al. | |
| 6,156,173 A * | 12/2000 | Gotoh et al. | 204/403.04 |
| 6,338,790 B1 | 1/2002 | Feldman et al. | |
| 6,591,125 B1 * | 7/2003 | Buse et al. | 600/347 |
| 6,605,200 B1 | 8/2003 | Mao et al. | |
| 6,605,201 B1 | 8/2003 | Mao et al. | |
| 6,764,581 B1 | 7/2004 | Forrow et al. | |
| 7,160,251 B2 | 1/2007 | Neel et al. | |
| 2004/0231984 A1 | 11/2004 | Lauks et al. | |
| 2006/0091006 A1 | 5/2006 | Wang et al. | |
| 2006/0144704 A1 | 7/2006 | Ghesquiere et al. | |
| 2008/0105024 A1 | 5/2008 | Creaven et al. | |

FOREIGN PATENT DOCUMENTS

| | | |
|---|---|---|
| DE | 103 43 477 A1 | 7/2004 |
| JP | 2003014684 | 1/2003 |
| JP | 2005257334 | 9/2005 |
| WO | WO 2006/042304 A1 | 4/2006 |

* cited by examiner

*Primary Examiner* — Thiem Phan
(74) *Attorney, Agent, or Firm* — Edward J. Baba; Marcus T. Hunt; Bozicevic, Field & Francis LLP

(57) ABSTRACT

Methods of making sensors, for determining the concentration of an analyte, such as glucose, in a biological fluid such as blood or serum, using techniques such as coulometry, amperometry, and potentiometry. The sensor includes a working electrode and a counter electrode, and may include an insertion monitoring trace to determine correct positioning of the sensor in a connector. The sensor is calibration-adjusted, eliminating the need for a user to enter a calibration code or for the meter to read a calibration code.

14 Claims, 3 Drawing Sheets

METHOD OF MAKING A PLURALITY OF CALIBRATION-ADJUSTED SENSORS

CROSS-REFERENCE TO RELATED APPLICATIONS

This application is a continuation of U.S. patent application Ser. No. 11/981,124, filed on Oct. 30, 2007, which is a divisional of U.S. patent application Ser. No. 11/461,725, filed on Aug. 1, 2006, which are incorporated herein by reference.

FIELD OF THE INVENTION

This invention relates to analytical sensors for the detection of analytes in a sample, and methods of making and using the sensors.

BACKGROUND

Biosensors, also referred to as analytical sensors or merely sensors, are commonly used to determine the presence and concentration of a biological analyte in a sample. Such biosensors are used, for example, to monitor blood glucose levels in diabetic patients.

As sensors continue to be used, there continues to be an interest in sensors that are easy to manufacture and easy for a patient to use.

SUMMARY

The present disclosure provides sensors and methods for the detection and quantification of an analyte in a sample. The sensors are configured to provide a clinically accurate analyte level reading, without the user having to enter a calibration code or the like that corresponds to the sensor. Embodiments of the sensor are provided, by the manufacturer of the sensors, with a configuration that provides a standardized calibration.

In general, certain embodiments of the invention include sensors for analysis of an analyte in a sample, e.g., a small volume sample, by, for example, coulometry, amperometry and/or potentiometry. The sensors include at least a working electrode and a counter electrode, which may be on the same substrate (e.g., co-planar) or may be on different substrates (e.g., facing). The sensors also include a sample chamber to hold the sample in electrolytic contact with the working electrode. A sensor of the invention may utilize a non-leachable or diffusible electron transfer agent and/or a redox mediator. The sensors may be configured for side-filling, tip-filling, or top-filling. In addition, in some embodiments, the sensor may be part of an integrated sample acquisition and analyte measurement device. An integrated sample acquisition and analyte measurement device may include a sensor and a skin piercing member, so that the device can be used to pierce the skin of a user to cause flow of a fluid sample, such as blood, that may then be collected by the sensor. In at least some embodiments, the fluid sample may be collected without moving the integrated sample acquisition and analyte measurement device.

Various embodiments of methods of making sensors, according to this disclosure, include providing a sample chamber and/or measurement zone having an electrode surface area that, when filled with a sample to be tested, provides a clinically accurate analyte level reading, without the user having to enter a calibration code or the like that corresponds to the sensor, into a meter that is used to read the sensor. In certain embodiments, the sample chamber and/or measurement zone volume may be modified, e.g., physically altered, during the manufacturing process of the sensor so that the resulting sensor meets a pre-determined calibration code or standard. In many embodiments, the physical altering of the sensor is the last step of the manufacturing process. In other methods, the area of the electrode(s) present in the sample chamber and/or measurement zone may be modified, e.g., physically altered, during the manufacturing process of the sensor so that the resulting sensor meets a pre-determined calibration code. In yet another method, prior to assembling the sensor, individual components or materials of the sensor could be tested; upon assembling of the sensors, the physical characteristics of the sensor may be modified as needed to compensate for the previously tested component variations to meet a pre-determined calibration code. Multiple calibration-adjusted sensors may be intermingled, without the need to record a calibration code, as all the sensors would have been physically altered to obtain the same calibration.

In some embodiments, at least one pre-sensor or test sensor is made and tested for its slope and y-intercept. Subsequent sensors would be adjusted accordingly to have the desired, pre-determined slope and y-intercept; the adjustment would be based on the slope and y-intercept from the pre-sensor or test sensor. In some embodiments, a number of test sensors (e.g., 10 or 100) may be made, their slope and y-intercept averaged, and that average is used to adjust the shape and/or size of a batch of sensors (e.g., 1,000 sensors, 50,000 sensors, or 1,000,000 sensors).

In certain embodiments, one particular method of forming a sensor, as described above, includes forming at least one working electrode on a first substrate and forming at least one counter or counter/reference electrode on a second substrate. A spacer layer is disposed on either the first or second substrates. The spacer layer defines a chamber into which a sample may be drawn and held when the sensor is completed. Chemistry for detecting one or more analytes may be present on the first or second substrate in a region that will be exposed within the sample chamber when the sensor is completed. The first and second substrates may then be brought together and spaced apart by the spacer layer with the sample chamber providing access to the at least one working electrode and the at least one counter or counter/reference electrode. The volume of the sample chamber, and optionally the volume of the measurement zone, may be adjusted so that the resulting sensor meets certain criteria.

Certain other embodiments include forming at least one working electrode on a first substrate and forming at least one counter or counter/reference electrode on the same, first substrate. One or two additional layers may be added to define a chamber into which a sample may be drawn and held when the sensor is completed. Chemistry may be present in a region that will be exposed within the sample chamber when the sensor is completed. The substrates may then be brought together, forming a sample chamber providing access to the at least one working electrode and the at least one counter or counter/reference electrode. In some embodiments, the volume of the sample chamber, and optionally the volume of the measurement zone, may be adjusted so that the resulting sensor meets certain criteria. Adjusting the volume of the sample chamber may or may not modify the electrode area. Additionally or alternately, in some embodiments, the surface area of the at least one working electrode and/or the at least one counter or counter/reference electrode are adjusted so that the resulting sensor meets certain criteria. Adjusting the electrode area may or may not modify the volume of the sample chamber.

These and various other features which characterize the invention are pointed out with particularity in the attached claims. For a better understanding of the invention, its advantages, and objectives obtained by its use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views.

DETAILED DESCRIPTION

In some currently available systems, a value indicative of the calibration code of a sensor is manually entered into the meter or other equipment, for example, by the user. Based on the calibration code, the meter uses one of several programs or parameters stored within the meter. In other currently available systems, the sensor calibration code is directly read by the meter or other equipment, thus not requiring input or other interaction by the user. These sensors, however, still have a calibration code associated with them, which includes slope and y-intercept values. The slope and y-intercept values are used to determine the analyte concentration based on the measured signal. The calibration code, whether inputted manually or automatically, is needed to standardize the analysis results received from non-standardized sensors. In other words, different sensors vary, e.g., from lot to lot, a sufficient amount that, if no compensation were made, the results would differ from sensor to sensor and the results could be clinically inaccurate.

The sensors of this disclosure are calibration-adjusted to a pre-determined calibration (slope and y-intercept), during the manufacturing process, to avoid the need for the user to input or otherwise set a calibration code for the sensor or perform other calibration procedure(s) before using the sensor. The sensors of this disclosure are also calibration-adjusted to avoid the need for the meter to read a calibration code.

It has been determined that the measured signal (e.g., charge due to electrooxidation or electroreduction) from the analyte in a sample is proportional to a physical element of the sensor. For example, when coulometry is used to obtain a signal proportionate to the analyte concentration, the signal obtained is proportional to the volume of sample being assayed. For amperometry or other kinematical electrolysis, the signal is proportion to the area of the electrode(s), e.g., the at least one working electrode, in the sample chamber. By physically altering the sensor's sample chamber volume or electrode area within the sample chamber during the manufacturing process, e.g., after the assembly of multiple layers, the slope and y-intercept of the sensor lot can be controlled, e.g., shifted, to provide a sensor with a pre-determined calibration. In some embodiments, the relationship between the sample chamber volume and the measured signal is linear. Additionally or alternatively, in some embodiments the relationship between the electrode area and the measured signal is linear.

This disclosure also provides methods for making sensors that avoid the need for the user to input or otherwise set a calibration code for the sensor, or perform other calibration procedure(s) before using the sensor.

Figure 1:
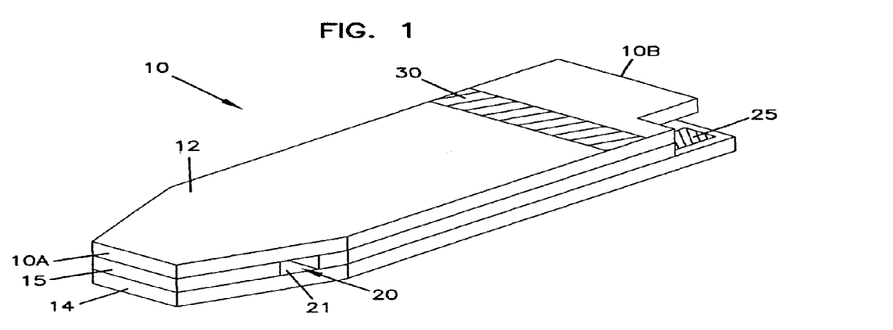
FIG. 1 is a schematic view of a first embodiment of a sensor strip in accordance with the present invention.
Figure 2:
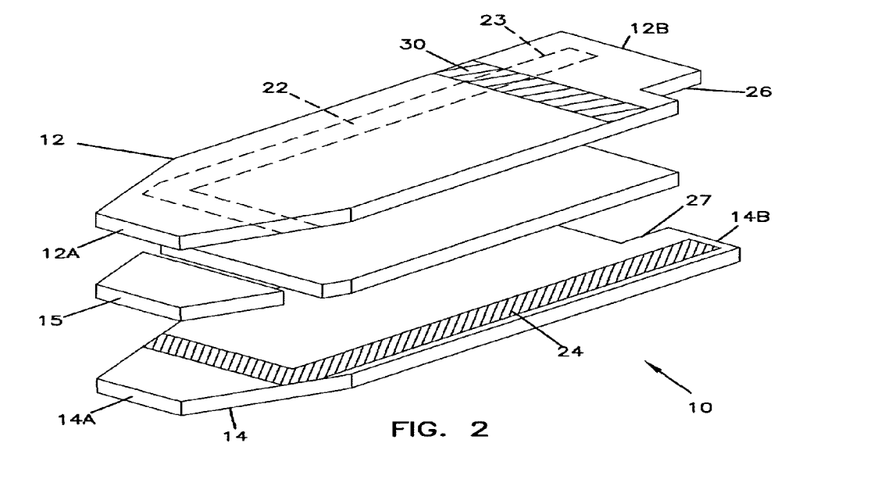
FIG. 2 is an exploded view of the sensor strip shown in FIG. 1, the layers illustrated individually with the electrodes in a first configuration.

Referring to the Drawings in general and FIGS. 1 and 2 in particular, a first embodiment of a sensor 10 is schematically illustrated, herein shown in the shape of a strip. It is to be understood that the sensor may be any suitable shape. Sensor strip 10 has a first substrate 12, a second substrate 14, and a spacer 15 positioned therebetween. Sensor strip 10 includes at least one working electrode 22 and at least one counter electrode 24. Sensor strip 10 also includes an optional insertion monitor 30.

Sensor strip 10 has a first, distal end 10A and an opposite, proximal end 10B. At distal end 10A, sample to be analyzed is applied to sensor 10. Distal end 10A could be referred as 'the fill end', 'sample receiving end', or similar. Proximal end 10B of sensor 10 is configured for operable, and usually releasable, connecting to a device such as a meter.

Sensor strip 10 is a layered construction, in certain embodiments having a generally rectangular shape, i.e., its length is longer than its width, although other shapes are possible as well, as noted above. The length of sensor strip 10 is from end 10A to end 10B.

The dimensions of a sensor may vary. In certain embodiments, the overall length of sensor strip 10 may be no less than about 10 mm and no greater than about 50 mm. For example, the length may be between about 30 and 45 mm; e.g., about 30 to 40 mm. It is understood, however that shorter and longer sensor strips 10 could be made. In certain embodiments, the overall width of sensor strip 10 may be no less than about 3 mm and no greater than about 15 mm. For example, the width may be between about 4 and 10 mm, about 5 to 8 mm, or about 5 to 6 mm. In one particular example, sensor strip 10 has a length of about 32 mm and a width of about 6 mm. In another particular example, sensor strip 10 has a length of about 40 mm and a width of about 5 mm. In yet another particular example, sensor strip 10 has a length of about 34 mm and a width of about 5 mm.

Figure 3:
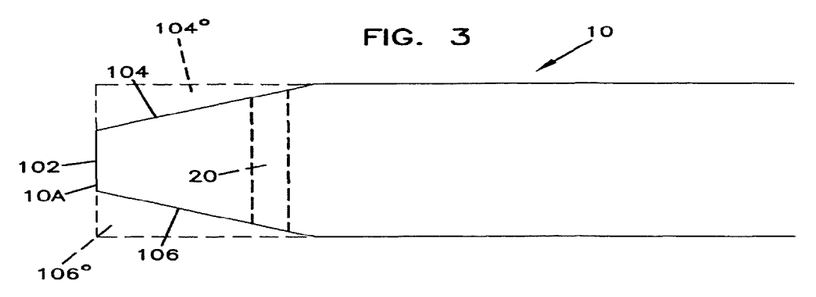
FIG. 3 is an enlarged top plan view of a portion of the sensor strip of FIG. 1.
Figure 4:
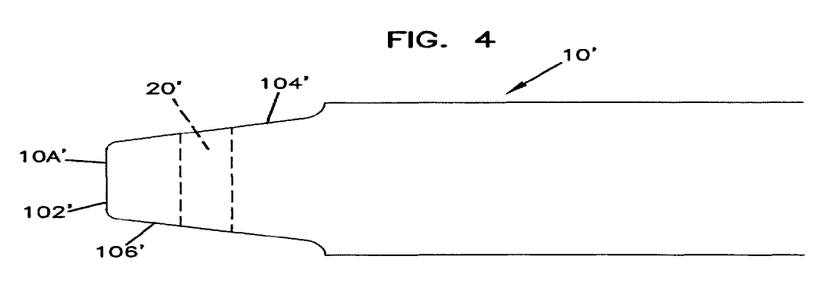
FIG. 4 is an enlarged top plan view of an alternate embodiment of a sensor strip, similar to FIG. 3.

Briefly referring to FIGS. 3 and 4, two different configurations of a portion of sensors are illustrated. FIG. 3 shows a portion of sensor strip 10 that includes first end 10A and sample chamber 20. FIG. 4 shows a portion of a sensor strip 10' that includes a sensor first end 10A' and a sample chamber 20'. The shape of sensors 10, 10' is the result of physically altering the sensor's measurement zone during the manufacturing process to provide sensor strips 10, 10' with predetermined calibration. Additional details are provided below.

Substrates and Spacer

As provided above, sensor strip 10 has first and second substrates 12, 14, non-conducting, inert substrates which form the overall shape and size of sensor strip 10. Substrates 12, 14 may be substantially rigid or substantially flexible. In certain embodiments, substrates 12, 14 are flexible or deformable. Examples of suitable materials for substrates 12, 14 include, but are not limited, to polyester, polyethylene, polycarbonate, polypropylene, nylon, and other "plastics" or polymers. In certain embodiments the substrate material is "Melinex" polyester. Other non-conducting materials may also be used.

Substrate 12 includes first or distal end 12A and second or proximal end 12B, and substrate 14 includes first or distal end 14A and second or proximal end 14B.

As indicated above, positioned between substrate 12 and substrate 14 may be spacer 15 to separate first substrate 12 from second substrate 14. In some embodiments, spacer 15 extends from end 10A to end 10B of sensor strip 10, or extends short of one or both ends. Spacer 15 is an inert non-conducting substrate, typically at least as flexible and deformable (or as rigid) as substrates 12, 14. In certain embodiments, spacer 15 is an adhesive layer or double-sided adhesive tape or film that is continuous and contiguous. Any adhesive selected for spacer 15 should be selected to not diffuse or release material which may interfere with accurate analyte measurement.

In certain embodiments, the thickness of spacer 15 may be constant throughout, and may be at least about 0.01 mm (10 µm) and no greater than about 1 mm or about 0.5 mm. For example, the thickness may be between about 0.02 mm (20 µm) and about 0.2 mm (200 µm). In one certain embodiment, the thickness is about 0.05 mm (50 µm), and about 0.1 mm (100 µm) in another embodiment.

Sample Chamber

The sensor includes a sample chamber for receiving a volume of sample to be analyzed; in the embodiment illustrated, particularly in FIG. 1, sensor strip 10 includes sample chamber 20 having an inlet 21 for access to sample chamber 20. In the embodiment illustrated, sensor strip 10 is a side-fill sensor strip, having inlet 21 present on a side edge of strip 10. Tip-fill sensors, having an inlet at, for example, end 10A, are also within the scope of this disclosure, as well as corner and top filling sensors.

Sample chamber 20 is configured so that when a sample is provided in chamber 20, the sample is in electrolytic contact with both a working electrode and a counter electrode, which allows electrical current to flow between the electrodes to effect the electrolysis (electrooxidation or electroreduction) of the analyte.

Sample chamber 20 is defined by substrate 12, substrate 14 and spacer 15; in many embodiments, sample chamber 20 exists between substrate 12 and substrate 14 where spacer 15 is not present. Typically, a portion of spacer 15 is removed to provide a volume between substrates 12, 14 without spacer 15; this volume of removed spacer is sample chamber 20. For embodiments that include spacer 15 between substrates 12, 14, the thickness of sample chamber 20 is generally the thickness of spacer 15.

Sample chamber 20 has a volume sufficient to receive a sample of biological fluid therein. In some embodiments, such as when sensor strip 10 is a small volume sensor, sample chamber 20 has a volume that is typically no more than about 1 µL, for example no more than about 0.5 µL, and also for example, no more than about 0.25 µL. A volume of no more than about 0.1 µL is also suitable for sample chamber 20, as are volumes of no more than about 0.05 µL and about 0.03 µL.

A measurement zone is contained within sample chamber 20 and is the region of the sample chamber that contains only that portion of the sample that is interrogated during the analyte assay. In some designs, the measurement zone has a volume that is approximately equal to the volume of sample chamber 20. In some embodiments the measurement zone includes 80% of the sample chamber, 90% in other embodiments, and about 100% in yet other embodiments.

As provided above, the thickness of sample chamber 20 corresponds typically to the thickness of spacer 15. Particularly for facing electrode configurations, as in the sensor illustrated in FIG. 2, this thickness is small to promote rapid electrolysis of the analyte, as more of the sample will be in contact with the electrode surface for a given sample volume. In addition, a thin sample chamber 20 helps to reduce errors from diffusion of analyte into the measurement zone from other portions of the sample chamber during the analyte assay, because diffusion time is long relative to the measurement time, which may be about 5 seconds or less.

Electrodes

As provided above, the sensor includes a working electrode and at least one counter electrode. The counter electrode may be a counter/reference electrode. If multiple counter electrodes are present, one of the counter electrodes will be a counter electrode and one or more may be reference electrodes.

For sensor 10, at least one working electrode is positioned on one of first substrate 12 and second substrate 14 in the measurement zone and/or sample chamber. In FIG. 2, working electrode 22 is illustrated on substrate 12. Working electrode 22 extends from the sample chamber 20, proximate distal end 10A, to the other end of the sensor 10, end 10B, as an electrode extension called a "trace". The trace provides a contact pad 23 for providing electrical connection to a meter or other device to allow for data and measurement collection, as will be described later. Contact pad 23 may be positioned on a tab 26 that extends from the substrate on which working electrode 22 is positioned, such as substrate 12. In some embodiments, a tab has more than one contact pad positioned thereon. In alternate embodiments, a single contact pad is used to provide a connection to one or more electrodes; that is, multiple electrodes are coupled together and are connected via one contact pad.

Working electrode 22 may be a layer of conductive material such as gold, carbon, platinum, ruthenium dioxide, palladium, or other non-corroding, conducting material. Working electrode 22 may be a combination of two or more conductive materials. An example of a suitable conductive epoxy is ECCOCOAT CT5079-3 Carbon-Filled Conductive Epoxy Coating (available from W.R. Grace Company, Woburn, Mass.). The material of working electrode 22 typically has relatively low electrical resistance and is typically electrochemically inert over the potential range of the sensor during operation.

Working electrode 22 may be applied on substrate 12 by any of various methods, including by being deposited, such as by vapor deposition or vacuum deposition or otherwise sputtered, printed on a flat surface or in an embossed or otherwise recessed surface, transferred from a separate carrier or liner, etched, or molded. Suitable methods of printing include screen-printing, piezoelectric printing, ink jet printing, laser printing, photolithography, and painting.

As provided above, at least a portion of working electrode 22 is provided in sample chamber 20 for the analysis of analyte, in conjunction with the counter electrode.

The sensor includes at least one counter electrode positioned within the measurement zone and/or sample chamber. In FIG. 2, counter electrode 24 is illustrated on substrate 14. In alternate embodiments, a counter electrode is present on a different surface or substrate, such as substrate 12. Counter electrode 24 extends from the sample chamber 20, proximate first end 10A, to the other end of the sensor 10, end 10B, as an electrode extension called a "trace". The trace provides a contact pad 25 for providing electrical connection to a meter or other device to allow for data and measurement collection, as will be described later. Contact pad 25 may be positioned on a tab 27 that extends from the substrate on which counter electrode 24 is positioned, such as substrate 12 or 14. In some embodiments, a tab has more than one contact pad positioned thereon. In alternate embodiments, a single contact pad is used to provide a connection to one or more electrodes; that is, multiple electrodes are coupled together and are connected via one contact pad.

Counter electrode 24 may be constructed in a manner similar to working electrode 22. Suitable materials for the counter/reference or reference electrode include Ag/AgCl or Ag/AgBr on a non-conducting base material or silver chloride on a silver metal base. The same materials and methods may be used for counter electrode 24 as are available for working electrode 22, although different materials and methods may also be used. Counter electrode 24 may include a mix of multiple conducting materials, such as Ag/AgCl and carbon.

Working electrode 22 and counter electrode 24 may be disposed opposite to and facing each other to form facing electrodes. See for example, FIG. 2, which has working electrode 22 on substrate 12 and counter electrode 24 on substrate 14, forming facing electrodes. In this configuration, the sample chamber is typically present between the two electrodes 22, 24. Working electrode 22 and counter electrode 24 may alternately be positioned generally planar to one another, such as on the same substrate, to form co-planar or planar electrodes.

In some instances, it is desirable to be able to determine when the sample chamber of the sensor is sufficiently filled with sample. Sensor strip 10 may be indicated as filled, or substantially filled, by observing a signal between an optional indicator electrode and one or both of working electrode 22 or counter electrode 24 as sample chamber 20 fills with fluid. When fluid reaches the indicator electrode, the signal from that electrode will change. Suitable signals for observing include, for example, voltage, current, resistance, impedance, or capacitance between the indicator electrode and, for example, working electrode 22. Alternatively, the sensor may be observed after filling to determine if a value of the signal (e.g., voltage, current, resistance, impedance, or capacitance) has been reached indicating that the sample chamber is filled.

Typically, the indicator electrode is further downstream from a sample inlet, such as inlet 21, than working electrode 22 and/or counter electrode 24.

For side-fill sensors, such as sensor 10 of FIGS. 1 and 2, an indicator electrode may be present on each side of the counter electrode. This permits the user to fill the sample chamber from either the left or right side with an indicator electrode disposed further upstream. This three-electrode configuration is not necessary. Side-fill sensors may also have a single indicator electrode and may include some indication as to which side should be placed in contact with the sample fluid.

The indicator electrode may also be used to improve the precision of the analyte measurements. The indicator electrode may operate as a working electrode or as a counter electrode or counter/reference electrode. Measurements from the indicator electrode/working electrode may be combined (e.g., added or averaged) with those from the first counter/reference electrode/working electrode to obtain more accurate measurements.

The sensor or equipment that the sensor connected is with (e.g., a meter) may include a signal (e.g., a visual sign or auditory tone) that is activated in response to activation of the indicator electrode to alert the user that the desired zone has been filled. The sensor or equipment may be configured to initiate a reading when the indicator electrode indicates that the measurement zone has been filled with or without alerting the user. The reading may be initiated, for example, by applying a potential between the working electrode and the counter electrode and beginning to monitor the signals generated at the working electrode.

Sensing Chemistry

In addition to working electrode 22, sensing chemistry material(s) are preferably provided in sample chamber 20 for the analysis of the analyte. Sensing chemistry material facilitates the transfer of electrons between working electrode 22 and the analyte in the sample. Any sensing chemistry may be used in sensor strip 10; the sensing chemistry may include one or more materials.

The sensing chemistry may be diffusible or leachable, or non-diffusible or non-leachable. For purposes of discussion herein, the term "diffusible" will be used to represent "diffusible or leachable" and the term "non-diffusible" will be used to represent "non-diffusible or non-leachable" and variations thereof. Placement of sensing chemistry components may depend on whether they are diffusible or not. For example, both non-diffusible and/or diffusible component(s) may form a sensing layer on working electrode 22. Alternatively, one or more diffusible components may be present on any surface in sample chamber 20 prior to the introduction of the sample to be analyzed. As another example, one or more diffusible component(s) may be placed in the sample prior to introduction of the sample into sample chamber 20.

The sensing chemistry generally includes an electron transfer agent that facilitates the transfer of electrons to or from the analyte. The electron transfer agent may be diffusible or non-diffusible, and may be present on working electrode 22 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes may be used for other analytes.

The electron transfer agent, whether it is diffusible or not, facilitates a current between working electrode 22 and the analyte and enables the electrochemical analysis of molecules. The agent facilitates the transfer electrons between the electrode and the analyte.

This sensing chemistry may, additionally to or alternatively to the electron transfer agent, include a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator may be a polymeric redox mediator or a redox polymer (i.e., a polymer having one or more redox species). Examples of suitable redox mediators and redox polymers are disclosed in U.S. Pat. No. 6,338,790, for example, and in U.S. Pat. Nos. 6,605,200 and 6,605,201.

If the redox mediator is non-diffusible, then the redox mediator may be present on working electrode 22 as a layer. In an embodiment having a redox mediator and an electron transfer agent, if the redox mediator and electron transfer agent are both non-leachable, then both components are on working electrode 22 as individual layers, or combined and applied as a single layer.

The redox mediator, whether diffusible or not, mediates a current between working electrode 22 and the analyte and enables the electrochemical analysis of molecules which may not be suited for direct electrochemical reaction on an electrode. The mediator functions as an agent to transfer electrons between the electrode and the analyte.

Insertion Monitor

The sensor may include an indicator to notify when proper insertion of the sensor into receiving equipment, such as a meter, has occurred. As seen in FIGS. 1 and 2, sensor strip 10 includes insertion monitor 30 on an exterior surface of one of substrates 12, 14, in the illustrated sensor, sensor 10. Insertion monitor 30 is configured and arranged to close an electrical circuit when sensor 10 is properly inserted into the meter connector.

Insertion monitor 30 may be a stripe extending across an exterior surface of sensor 10, for example, from side edge to side edge, with one contact pad for connection to a meter. It is understood that in alternate embodiments of the insertion monitor, the stripe need not extend to both side edges. In other embodiments, the insertion monitor may be two or more contact pads for connection to a meter. The two or more contact pads could electrically connected to each other by a material, such as a conductive ink.

Insertion monitor 30 can be used to encode information regarding sensor strip 10. The encoded information may be, for example, the test time needed for accurate analyte concentration analysis, the expiration date of sensor strip 10, various correction factors, such as for environmental temperature and/or pressure, selection of the analyte to be analyzed (e.g., glucose, ketone, lactate), and the like. Additionally, insertion monitor 30 can be used to encode calibration information for the sensor, e.g., for the manufacturing lot or that specific sensor strip. However, in accordance with this disclosure, the sensor requires no calibration code; rather, the sensor is configured with a pre-determined calibration, based on the volume of the measurement zone.

Additional details regarding insertion monitors, and their use for encoding information, are described, for example, in U.S. Patent application publication no. 2006/0091006 A1. Additionally, U.S. Patent application publication no. 2006/0091006 A1 provides various details regarding connection of sensors with insertion monitors with meters and connectors.

Figure 5:
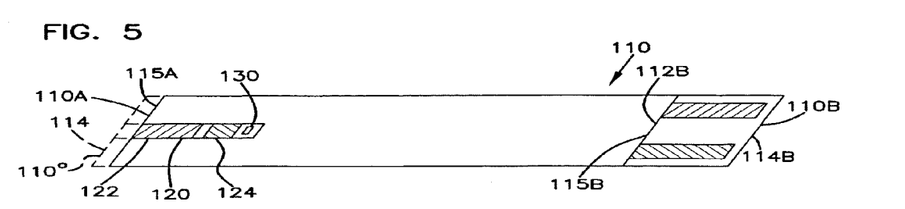
FIG. 5 is a schematic view of a third embodiment of a sensor strip in accordance with the present invention.
Figure 6:
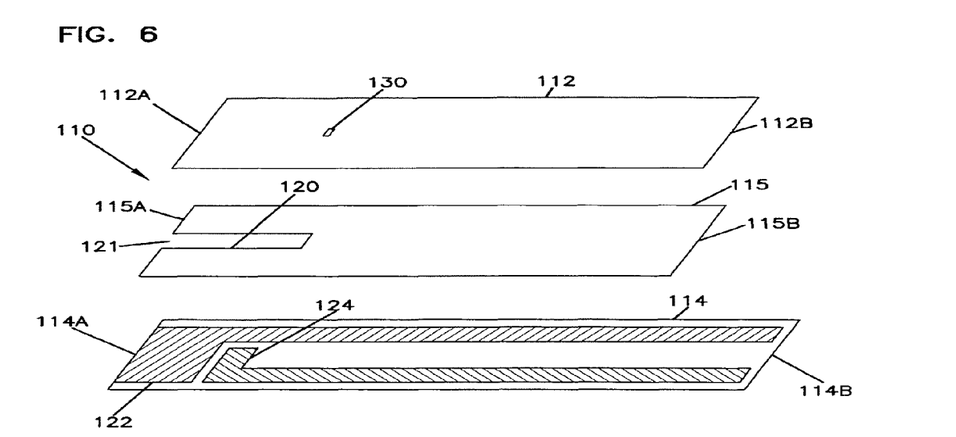
FIG. 6 is an exploded view of the sensor strip shown in FIG. 5, the layers illustrated individually with the electrodes in a first configuration.

Referring to FIGS. 5 and 6 in particular, an alternate embodiment of a sensor is illustrated as sensor strip 110. Similar to sensor strip 10, sensor strip 110 has a first substrate 112, a second substrate 114, and a spacer 115 positioned therebetween. Sensor strip 110 includes at least one working electrode 122 and at least one counter electrode 124.

Sensor strip 110 has a first, distal end 110A and an opposite, proximal end 110B. At distal end 110A, sample to be analyzed is applied to sensor 110. Distal end 110A could be referred as 'the fill end', 'sample receiving end', or similar. Proximal end 110B of sensor 110 is configured for operable, and preferably releasable, connecting to a device such as a meter. Similar to sensor strip 10, sensor strip 110 is a layered construction, in certain embodiments having a generally rectangular shape, which is formed by first and second substrates 112, 114. Substrate 112 includes first or distal end 112A and second or proximal end 112B, and substrate 114 includes first or distal end 114A and second or proximal end 114B. The discussion above about substrates 12, 14 and spacer 15 applies to substrates 112, 114 and spacer 15.

Sensor strip 110 includes sample chamber 120 having an inlet 121 for access to sample chamber 120. Sensor strip 110 is a tip-fill sensor, having inlet 121 at end 110A.

Similar to sample chamber 20 of sensor strip 10, sample chamber 120 is defined by substrate 112, substrate 114 and spacer 115. Generally opposite to inlet 121, through substrate 112 is a vent 130 from sample chamber 120. The discussion above about sample chamber 20 and its measurement zone applies to sample chamber 120.

For sensor 110, at least one working electrode 122 is illustrated on substrate 114. Working electrode 122 extends from end 114A into sample chamber 120 to end 114B and 110B. Sensor 110 also includes at least one counter electrode 124, in this embodiment on substrate 114. Counter electrode 124 extends from sample chamber 120, proximate first end 110A, to end 110B, as an electrode extension called a "trace". Working electrode 122 and counter electrode 124 are present on the same substrate e.g., as planar or co-planar electrodes. The electrodes 122, 124 may include sensing chemistry material(s) thereon.

General Method for Manufacturing Sensors

Sensor strips 10, 110 discussed above, are sandwiched or layered constructions having substrates 12, 14, 112, 114 spaced apart, such as by spacer 15, 115. Such a construction may be made by laminating the various layers together, in any suitable manner. An alternate method for making sensor strips 10, 110, and other sensors in accordance with the invention, is to mold the sensors.

Molding may include positioning at least two spaced apart electrically conductive electrodes (e.g., wires) in a mold, and molding a body of insulative material around the electrodes, with one end having therein means for receiving a fluid sample. More specifically, molding could include positioning at least two spaced apart electrically conductive electrodes (e.g., wires) in a mold, before or after molding, treating at least one of the electrodes with one or more chemicals to change the electrical properties of the treated electrode upon contact with a fluid sample, and molding a body of insulative material around the electrodes with one end having therein means for receiving a fluid sample. The body may be molded in multiple pieces, e.g., two pieces, with a body and end cap for attaching to one another after the molding is completed, or in a single piece.

A sensor may be made by positioning electrodes on one or more substrates, the substrates including a first substrate, optionally contacting at least a portion of at least one electrode with sensing material(s), and configuring the sensor by positioning a spacer between the two substrates to maintain the substrates in a fixed, layered orientation relative to each other.

Calibration of Sensors

Whether the sensors are laminated, molded, or made by some other process, after or during forming the sensor, a portion of the sensor is physically modified (e.g., removed, re-shaped, reacted, etc.) to provide the sensor with a pre-determined slope and y-intercept. Typically, the physically modified portion of the sensor includes the sample chamber and/or measurement zone. In accordance with some embodiments of this disclosure, the sample chamber shape and/or size is altered to provide the sensor with the desired pre-determined slope and y-intercept. In many embodiments, the shape and/or size of the sample chamber and/or measurement zone is physically modified. Additionally or alternately, in accordance with some embodiments of this disclosure, the electrode area within the sample chamber and/or measurement zone is altered, sometimes without altering the sample chamber shape and/or size. In many embodiments, the electrode area is physically modified.

Referring again to FIGS. 3 and 4, two different configurations of sensors are illustrated. FIG. 3 shows a portion of sensor strip 10 that includes first end 10A and FIG. 4 shows a portion of a sensor strip 10' that includes a sensor first end 10A'. Sensor strip 10 includes first edge 102 (which in this embodiment is also sensor end 10A), second edge 104 and third edge 106, each of which is a straight, linear edge. The corners formed by the meeting of edges 104, 106 with edge 102 are angular, in this embodiment, having an internal angle of about 108 degrees. In this embodiment, sample chamber 20 extends across sensor strip 10 from edge 104 to edge 106. Sensor strip 10' includes first edge 102' (which in this embodiment is also sensor end 10A'), second edge 104' and third edge 106'. Edges 104' and 106' are arcuate edges. Additionally, the corners formed by the meeting of edges 104', 106' with edge 102' are rounded or radiused. Also in this embodiment, sample chamber 20' extends across sensor 10' from edge 104' to edge 106'. The volume of sample chamber 20, 20' is defined by side edges 104, 104' and 106, 106' and the thickness of the sample chamber.

To clarify understanding, the following discussion will use the term "pre-sensor" when referring to the sensor prior to any physical alteration of the sensor.

Sensors 10, 10' are the result of physically altering the sample chamber and/or measurement zone after the manufacturing process of the pre-sensor to provide sensors that have a pre-determined slope and y-intercept. In some embodiments, "physically altering" includes removing a portion of the sample chamber and/or measurement zone of the pre-sensor. FIG. 3 illustrates a first phantom portion $104^\circ$ (i.e., 104 superscript naught), which corresponds to the portion of the pre-sensor removed to form edge 104, and a second phantom portion $106^\circ$ (i.e., 106 superscript naught), which corresponds to the portion of the pre-sensor removed to form edge 106. By removing phantom portions $104^\circ$, $106^\circ$, a portion of the sample chamber, i.e., that present in portions $104^\circ$, $106^\circ$, is also removed, thus physically altering the pre-sensor. For sensors 10, 10' of FIGS. 3 and 4, the calibration code is proportional to the volume of the measurement zone and/or the sample chamber of the sensor.

Referring to FIG. 5, sensor 110 is the result of physically altering the electrode area and the sample chamber and/or measurement zone after the manufacturing process of the pre-sensor to provide sensors that have a pre-determined slope and y-intercept. FIG. 5 illustrates phantom portion $110^\circ$ (i.e., 110 superscript naught), which corresponds to the portion of the pre-sensor removed to form edge 110A. By removing phantom portion $110^\circ$, a portion of the working electrode 122, i.e., that present on substrate 114 within phantom portion $110^\circ$, is also removed, thus physically altering the pre-sensor. For sensor 110 above, the calibration slope and y-intercept are proportional to the area of the electrode(s), e.g., working electrode 122, in the sample chamber of the sensor. In this embodiment, the volume of the sample chamber is reduced, due to the removal of phantom portion $110^\circ$. It is noted that in alternate embodiments, the sample chamber volume and/or measurement zone volume may remain the same although the area of the electrodes is modified. One exemplary method for modifying the electrode area, e.g., removing area, is by the use of non-invasive procedures, such as a single or multiple energy beams (e.g., lasers, UV light, electron beam, etc.) that pass through the inert substrates but physically alter the electrodes. In this process, areas of electrode(s) may be removed or otherwise rendered inactive.

To provide a plurality of sensors, such as sensor strips 10, 10', 110 with the same pre-determined calibration from a plurality of pre-sensors, each of the pre-sensors may be physically altered, as needed, to obtain the desired pre-determined physical characteristics and the desired sensor. It is understood that this discussion also applies to a batch or lot of sensors in addition to a single sensor. For example, a first pre-sensor may have a response that is too high compared to the desired level and a second pre-sensor may have a response that is within the desired level. In such a situation, a portion of the first pre-sensor may be removed to provide a sensor having a measurement zone, sample chamber, or electrode area that is comparable to that of the second pre-sensor and is within the desired level.

In some situations, however, a pre-sensor, e.g., a third sensor strip, may have a response that is too low compared to the desired level. Because in most embodiments it would be difficult or impractical to increase the measurement zone, sample chamber, and/or electrode area of the pre-sensor after it has been assembled, in some manufacturing operations the desired response level may be artificially lowered in order to pre-calibrate the sensor. With such an artificially lowered desired level, for a pre-sensor that has a response within that desired artificially low level, a pre-determined portion of the pre-sensor's active area may be removed to obtain a sensor with the actual desired level; for a pre-sensor that has a response above the desired artificially low, a larger portion than the pre-determined portion of the pre-sensor's active area may be removed to obtain a sensor with the actual desired level; and for a pre-sensor that has a response below the desired artificially low level, a smaller portion than the pre-determined portion of the pre-sensor's active area is removed in order to obtain a sensor with the actual desired level. In other words, using such a methodology, all the pre-sensors would be physically altered to obtain sensors with the same desired pre-determined calibration.

The pre-sensor is modified in order to obtain the desired pre-determined calibration, either by altering the volume of the sample chamber and/or measurement zone or by the electrode area in the sample chamber. Referring to FIGS. 3 and 4, in this embodiment, the volume of the sample chamber and/or measurement zone is modified by removing phantom portions $104^\circ$, $106^\circ$, and the electrode area is modified in FIG. 5 by removing phantom portion $110^\circ$.

In some embodiments, there may be no actual pre-sensor that is subsequently modified to form the sensor, but rather, a pre-sensor is used as a template for one or more sensors (e.g., batch or lot of sensors, e.g., at least 100 sensors, at least 1,000 sensors, or even at least 50,000 sensors). For example, multiple sensors may be obtained from, e.g., a large sheet construction having working electrodes, counter electrodes and sample chambers. See for example, U.S. Pat. No. 6,338,790, particularly FIGS. 31A and 31B and the description associated therewith, which describes methods of making a plurality of sensors from a large sandwiched sheet construction. From this sheet, one (or more) test sensors could be removed (e.g., punched) using a standard template (e.g., shape and size), and these test sensors could be tested for their difference from the desired slope and y-intercept, and the results typically averaged. Subsequently removed sensors would be modified from the test sensor, as needed, by removing (e.g., punching) an appropriately shaped and sized sensor, which may differ from the test sensors, to obtain the desired slope and y-intercept. In this method, the test sensors provide a guide for the modification needed, so that each sensor is not individually tested.

It is understood that other configurations of phantom portions would be suitable. For example, sensor 10 of FIG. 3 has edge 102 and edges 104, 106 forming an angle of about 108 degrees. This corner angle could be about 90 degrees or be a high as 180 degrees; in most embodiments, however, this corner angle is in the range of about 90 to about 145 degrees. Angles less than 90 degrees could be used for a concave edge 102, 102'. The corners could be sharp, as in FIG. 3, or rounded, as in FIG. 4. Any or all of edges 102, 104, 106 may be straight or curved, with concave, convex, or a combination of shapes. Both sensor strips 10, 10' have edge 102, 102' forming end 10A, 10A'; in alternate embodiments, the sensor end could be defined by the meeting of edges 104, 106 (i.e., the side edges meet at a point with no end edge). In some embodiments, the sensor could be asymmetrical, e.g., having only one portion removed from the sensor. Other shapes for sensors would be suitable. FIGS. 5 and 6 illustrate sensor strip 110 with a blunt end 110A, having 90 degree corners. After providing any of sensors 10, 10', 110, the proximal ends, e.g., 10B, 10B could be adjusted so that all sensors in the lot have the same final size.

Application of the Sensor

A common use for a sensor of the present invention, such as sensor strip 10, 10' 110, is for the determination of analyte concentration in a biological fluid, such as glucose concentration in blood, interstitial fluid, and the like, in a patient or other user. Additional analytes that may be determined include but are not limited to, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Sensors may be available at pharmacies, hospitals, clinics, from doctors, and other sources of medical devices. Multiple sensors may be packaged together and sold as a single unit; e.g., a package of about 25, about 50, or about 100 sensors, or any other suitable number. A kit may include one or more sensors, and additional components such as control solutions and/or lancing device and/or meter, etc.

Sensors may be used for an electrochemical assay, or, for a photometric test. Sensors are generally configured for use with an electrical meter, which may be connectable to various electronics. A meter may be available at generally the same locations as the sensors, and sometimes may be packaged together with the sensors, e.g., as a kit.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touchscreen. With such an arrangement, the user can control the meter indirectly by interacting with the user interface(s) of the server device, which in turn interacts with the meter across a wireless link.

The server device may also communicate with another device, such as for sending data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as the sensors and the meter, and sometimes may be packaged together with the sensor and/or meter, e.g., as a kit.

The sensors are particularly suited for inclusion in an integrated device, i.e., a device which has the sensor and a second element, such as a meter or a lancing device, in the device. The integrated device may be based on providing an electrochemical assay or a photometric assay. In some embodiments, sensors may be integrated with both a meter and a lancing device. Having multiple elements together in one device reduces the number of devices needed to obtain an analyte level and facilitates the sampling process. For example, embodiments may include a housing that includes one or more of the sensor strips, a skin piercing element and a processor for determining the concentration of an analyte in a sample applied to the strip. A plurality of sensors may be retained in a cassette in the housing interior and, upon actuation by a user, a single sensor may be dispensed from the cassette so that at least a portion extends out of the housing for use.

Operation of the Sensor Strip

In use, a sample of biological fluid is provided into the sample chamber of the sensor, where the level of analyte is determined. The analysis may be based on providing an electrochemical assay or a photometric assay. In many embodiments, it is the level of glucose in blood that is determined. Also in many embodiments, the source of the biological fluid is a drop of blood drawn from a patient, e.g., after piercing the patient's skin with a lancing device, which could be present in an integrated device, together with the sensor strip.

Prior to providing the sample to the sensor, or even after providing the sample to the sensor, there is no need for the user to input a calibration code or other information regarding the operation and/or interaction of the sensor with the meter or other equipment. The sensor is configured so that the results received from the analysis are clinically accurate, without the user having to adjust the sensor or the meter. The sensor is physically configured to provide accurate results that are repeatable by a batch of sensors.

After receipt of the sample in the sensor, the analyte in the sample is, e.g., electrooxidized or electroreduced, at the working electrode and the level of current obtained at the counter electrode is correlated as analyte concentration. The sensor may be operated with or without applying a potential to the electrodes. In one embodiment, the electrochemical reaction occurs spontaneously and a potential need not be applied between the working electrode and the counter electrode. In another embodiment, a potential is applied between the working electrode and the counter electrode.

The invention has been described with reference to various specific and preferred embodiments and techniques. However, it will be apparent to one of ordinarily skill in the art that many variations and modifications may be made while remaining within the spirit and scope of the invention. It is understood that elements or features present on one embodiment described above could be used on other embodiments. For example, the discussion above has been directed to modifying the sensor based on an output (e.g., charge) from an assembled sensor. In an alternate embodiment, individual components or materials of the sensor could be tested prior to assembling the sensor, and then modifying the sensor as needed to compensate for the previous test. For example, the sensing chemistry activity may be tested prior to incorporation of the chemistry in a sensor. If, for example, the activity is below the desired standard, when incorporated into sensor, the sensors could be physically adjusted (e.g., sample chamber volume or electrode area increased) to compensate for the low chemistry activity. Similarly, if the activity is above the desired standard, when incorporated into sensor, the sensors could be physically adjusted (e.g., sample chamber volume or electrode area decreased) to compensate for the high chemistry activity.

Experimental

Five sensor strips, each having a distal end similar to that illustrated in FIG. 4, were punched from a laminated sheet composed of two substrates and a spacer layer therebetween, with at least one working electrode and at least one counter electrode in facing configuration. Each of the sensor strips had arcuate edges, similar to edges 104', 106' in FIG. 4. The table below provides parameters for the five sensor strips. The "tip distance" was the distance between the distal most end of the sensor strip (e.g., end 10A' in FIG. 4) and the sample chamber (e.g., sample chamber 20' in FIG. 4). The punch that formed the distal end and the arcuate edges was the same punch for each of the sensor strips. Thus, as the distance between the tip and the sample chamber increased, the length of the sample chamber (between the arcuate edges) increased, thus increasing the sample chamber volume.

| Tip distance (0.001 inch) | Sample chamber volume (nanoliter) | Charge (microcoulombs) |
| --- | --- | --- |
| 10 | 97 | 98.7 |
| 20 | 103 | 107.7 |
| 30 | 109 | 115.9 |
| 40 | 114 | 123.4 |
| 50 | 120 | 127.9 |

This data shows a linear relationship between the sample chamber volume and the measured charge; the linear equation is $y=1.3x-26.4$. Also, the data shows a linear relationship between the tip distance and the measured charge; the linear equation is $y=0-0.74x+92.5$. With this knowledge, the punch position to achieve the desired sensor response for this batch of sensors can be calculated.

All patents and other references in this specification are indicative of the level of ordinary skill in the art to which this invention pertains. All patents and other references are herein incorporated by reference to the same extent as if each individual patent or reference was specifically and individually incorporated by reference.

What is claimed:

1. A method of making a plurality of calibration-adjusted sensors for use in determining a concentration of a ketone body in a sample, the method comprising:
   (a) providing a plurality of pre-sensors, each pre-sensor comprising a working electrode, a counter electrode, and a sample chamber, wherein the sample chamber has at least part of the working electrode and the counter electrode arranged therein, wherein the plurality of pre-sensors include at least a first pre-sensor and a second pre-sensor;
   (b) physically modifying the first pre-sensor to form a first sensor, the first sensor having a first physical characteristic defining a first slope and a first y-intercept;
   (c) determining the first slope and the first y-intercept of the first sensor;
   (d) comparing the first slope of the first sensor to a first desired slope and comparing the first and y-intercept of the first sensor to a first desired y-intercept; and
   (e) physically modifying the second pre-sensor to form a second sensor having a second physical characteristic defining a second slope and a second y-intercept of the second sensor such that the second slope of the second sensor is substantially equal to the first desired slope and such that the second y-intercept of the second sensor is substantially equal to the first desired y-intercept.

2. The method of claim 1, further comprising:
   forming a third sensor by physically modifying a third pre-sensor of the plurality of pre-sensors subsequent to such that the third sensor has a third physical characteristic defining a third slope and a third y-intercept that is substantially equal to the first desired slope and the first desired y-intercept/being substantially equal to the desired slope and y-intercept.

3. The method of claim 1, wherein the second sensor is physically different than the first sensor.

4. The method of claim 1, further comprising physically modifying at least 99 additional pre-sensors of the plurality of pre-sensors to form at least 99 additional sensors having physical characteristics defining slopes and y-intercepts that are substantially equal to the first desired slope and the first desired y-intercept.

5. The method of claim 1, wherein providing a plurality of pre-sensors further comprises:
   providing a first substrate having the plurality of working electrodes thereon;
   providing a spacer layer over the first substrate; and
   overlaying the spacer layer with a second substrate.

6. The method of claim 1, wherein the sensor is a tip-fill sensor, a side-fill sensor, corner-fill sensor, or a top-fill sensor.

7. The method of claim 1, wherein physically modifying the first pre-sensor and the second pre-sensor comprises modifying a volume of the sample chamber.

8. The method of claim 1, wherein physically modifying the first pre-sensor and the second pre-sensor comprises modifying an electrode area in the sample chamber.

9. The method of claim 1, wherein at least the first slope and the first y-intercept of are different than the second slope and the second y-intercept.

10. The method of claim 1, wherein the first physical characteristic is a first size of the sample chambers of the first sensor and wherein the second physical characteristics is a second size of the sample chamber of the second sensor.

11. The method of claim 1, wherein the physically modifying the first and second pre-sensors comprises modifying a size of the first and second pre-sensor sample chambers.

12. The method of claim 1, wherein the first and second physical characteristics relate to at least one of the working electrode and the counter electrode of the first and second sensors.

13. The method of claim 1, wherein physically modifying the first and second pre-sensors comprises modifying a size of the working electrode and counter electrode of the first and second pre-sensors.

14. The method of claim 1, wherein physically modifying the first and second pre-sensors comprises modifying at least one of the sample chamber, a measurement zone, and electrode configuration, an electrode dimension, an enzyme, a mediators, a polymer, a chemistry concentration, and any combination thereof.

* * * * *

UNITED STATES PATENT AND TRADEMARK OFFICE
CERTIFICATE OF CORRECTION

| | | |
|---|---|---|
| PATENT NO. | : 7,996,988 B2 | Page 1 of 1 |
| APPLICATION NO. | : 12/463192 | |
| DATED | : August 16, 2011 | |
| INVENTOR(S) | : Yi Wang | |

It is certified that error appears in the above-identified patent and that said Letters Patent is hereby corrected as shown below:

In Column 15, line 42, please replace "y=0–0.74" with --y=–0.74--.

In Column 16, line 2, claim 1, please replace "first and y-intercept" with --first y-intercept--.

In Column 16, line 13, claim 2, please delete "subsequent to".

In Column 16, lines 17-18, claim 2, please delete "/being substantially equal to the desired slope and y-intercept".

In Column 16, line 41, claim 9, please delete "at least".

In Column 16, line 42, claim 9, please delete "of".

In Column 16, line 45, claim 10, please replace "chambers" with --chamber--.

In Column 16, line 46, claim 10, please replace "characteristics" with --characteristic--.

In Column 16, line 48, claim 11, please replace "wherein the physically" with --wherein physically--.

In Column 16, line 57, claim 13, please replace "and counter electrode" with --and the counter electrode--.

In Column 16, line 61, claim 14, please replace "and" with --an--.

In Column 16, line 63, claim 14, please replace "mediators" with --mediator--.

Signed and Sealed this
Tenth Day of January, 2012

David J. Kappos
*Director of the United States Patent and Trademark Office*